United States Patent [19]
Evans

[11] Patent Number: 5,519,158
[45] Date of Patent: May 21, 1996

[54] METHOD AND APPARATUS FOR DESICCANT DRYING OF FLUOROSILICONES

[75] Inventor: Edwin R. Evans, Clifton Park, N.Y.

[73] Assignee: General Electric Company, Waterford, N.Y.

[21] Appl. No.: 342,982

[22] Filed: Nov. 21, 1994

Related U.S. Application Data

[62] Division of Ser. No. 174,581, Dec. 28, 1993, which is a continuation of Ser. No. 803,262, Dec. 5, 1991, abandoned.

[51] Int. Cl.$^6$ ..................................................... C07F 7/08
[52] U.S. Cl. ............................................ 556/460; 556/461
[58] Field of Search ..................................... 556/460, 461

[56] References Cited

U.S. PATENT DOCUMENTS

| | | |
|---|---|---|
| 3,481,898 | 12/1969 | Davies et al. . |
| 3,691,251 | 9/1972 | Bauer . |
| 4,122,247 | 10/1978 | Evans . |
| 4,551,515 | 11/1985 | Herbrg et al. . |
| 4,620,023 | 10/1986 | Kreuzer et al. ........................ 556/460 |
| 4,780,519 | 10/1988 | Saam et al. . |
| 4,835,326 | 5/1989 | Daren et al. . |
| 4,874,881 | 10/1989 | Suzuki et al. . |
| 4,876,373 | 10/1989 | Okawa et al. . |
| 5,130,399 | 7/1992 | Ikeno et al. . |
| 5,383,383 | 1/1995 | Legrow et al. ..................... 556/461 X |
| 5,403,945 | 4/1995 | Kishita et al. ........................ 556/460 |

FOREIGN PATENT DOCUMENTS

| | | |
|---|---|---|
| 0266076 | 5/1988 | European Pat. Off. . |
| 0265780 | 5/1988 | European Pat. Off. . |
| 2737698 | 10/1978 | Germany . |
| 2052539 | 1/1981 | United Kingdom . |

*Primary Examiner*—Paul F. Shaver

[57] ABSTRACT

A method of polymerizing organosiloxane monomers to produce high molecular weight polymers having a relatively narrow range of molecular weights, which includes drying the monomers to a selected moisture content of 10 ppm or less by moisture transfer contact with a desiccant at temperatures below the polymerization temperature prior to polymerization.

5 Claims, 3 Drawing Sheets

TO POLYMERIZATION STAGE

METHOD AND APPARATUS FOR DESICCANT DRYING OF FLUOROSILICONES

This is a divisional of application Ser. No. 08/174,581 filed on Dec. 28, 1993 which is a continuation of application Ser. No. 07/803,262 filed on Dec. 05, 1991 now abandoned.

FIELD OF THE INVENTION

The present invention relates to a process for drying organosiloxane monomers prior to polymerization and, more specifically, to a method and apparatus for desiccant drying of cyclic diorganosiloxane and halogen bearing diorganosiloxane monomers prior to polymerization.

BACKGROUND OF THE INVENTION

The polymerization of cyclic diorganosiloxanes to high molecular weight polymers requires that the monomer first be dried. It is preferred that the moisture level be reduced to a level which minimizes the amount of silanol end groups formed on the polymer chain ends. Evans, U.S. Pat. No. 4,122,247 discloses a process for the polymerization of cyclic diorganosiloxanes with cation-complex catalysts in which it is preferred that there be present less than 10 ppm of water in the composition of cyclic siloxanes which is to be used with the catalyst to make the polymers. Removal of all but traces of water is accomplished by heating to 100° C. or above with a nitrogen purge. According to the patent, this effectively reduces the water content of the cyclic siloxane composition to less than 10 ppm. If there is substantially more than this amount of water present in the cyclic siloxanes, then the desired low molecular weight oil or high molecular weight diorganosiloxane homo or copolymer gum will not be formed in commercially attractive yields. In essence, Evans raises the temperature of the material above the boiling point of water to drive off the excess water by distillation.

Saam et al., U.S. Pat. No. 4,780,519 discloses a method of producing polydiorganosiloxane gum in which azeotropic drying is employed to reduce the water level. This is accomplished by controlling the water vapor pressure in the reaction container. In particular, the reaction container is sealed so that the atmosphere can be controlled at a desired water vapor level. According to Saam, water vapor pressure is regulated by means of water vapor control of a nitrogen sweep during polymerization. A dew point meter placed at the exit stream of the reaction container is used to determine the amount of water vapor pressure present in the reaction container. By control of the dew point, that is, by the control of the amount of water carried by the nitrogen into the vessel, the amount of water in the reaction can be controlled. Saam also mentions that distillation techniques are available but not satisfactory.

The various methods discussed in Saam are deficient in a number of ways. Drying and polymerization occur simultaneously. Thus, the heating step may cause premature polymerization which can result in poor product yield. The various methods require additional apparatus to achieve the desired results. Further, unless the variables such as, for example, time, temperature and dew point are strictly controlled, such known processes may not achieve satisfactory results.

The moisture content in the reaction is controlled to minimize the amount of silanol end groups and to control the desired or target molecular weight range. The nature of the end groups and the molecular weight are controlled by the addition of chain stoppers such as:

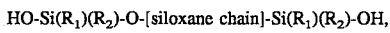

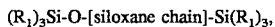

or

where

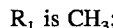$R_1$ is $CH_3$;

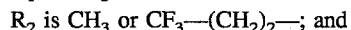$R_2$ is $CH_3$ or $CF_3$—$(CH_2)_2$—; and

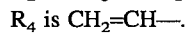$R_4$ is $CH_2$=$CH$—.

It is known that high molecular weight (HMW) polymers can be derived without drying from cyclic siloxanes, in particular from 1,3,5-trimethyl-1,3,5-tris(3,3,3-trifluoropropyl) cyclotrisiloxane to provide gums with a Williams Plasticity (WP) (3') of <200. The value can be increased by azeotropically drying the polymer prior to polymerization. However, azeotropic drying is inefficient and does not result in the desired degree of control of the resulting high molecular weight range. A narrow range of molecular weight has a positive effect upon the producibility and quality of resulting compounds, for example heat cured rubbers. Distillation and azeotropic drying, while effective to produce a water level thought to be necessary in this art, nevertheless result in shortcomings, both in terms of cost and quality of the product.

SUMMARY OF THE INVENTION

The present invention is directed to a method of polymerizing organosiloxane monomers to produce high molecular weight polymers. In a particular embodiment the method includes drying the monomers to a selected moisture content of 10 ppm or less by moisture transfer contact with a desiccant at temperatures below the polymerization temperature of the monomers, thereby minimizing the formation of silanol end groups. The dry monomers are combined with selected amounts of chain stoppers for determining molecular weight, and the monomers and chain stoppers are heated to an elevated temperature above the polymerization temperature so as to result in formation of high molecular weight polymers having a relatively narrow range of molecular weights with a dispersion index less than about 1.8 relative to a target value, preferably less than 1.5 and more preferably about 1.2.

Various apparatus may be employed to implement the process including batch processing by continuous circulation from a holding tank through the desiccant or once through apparatus which include reaction columns containing a sufficient quantity of desiccant.

DESCRIPTION OF THE PREFERRED EMBODIMENT

Figure 1:
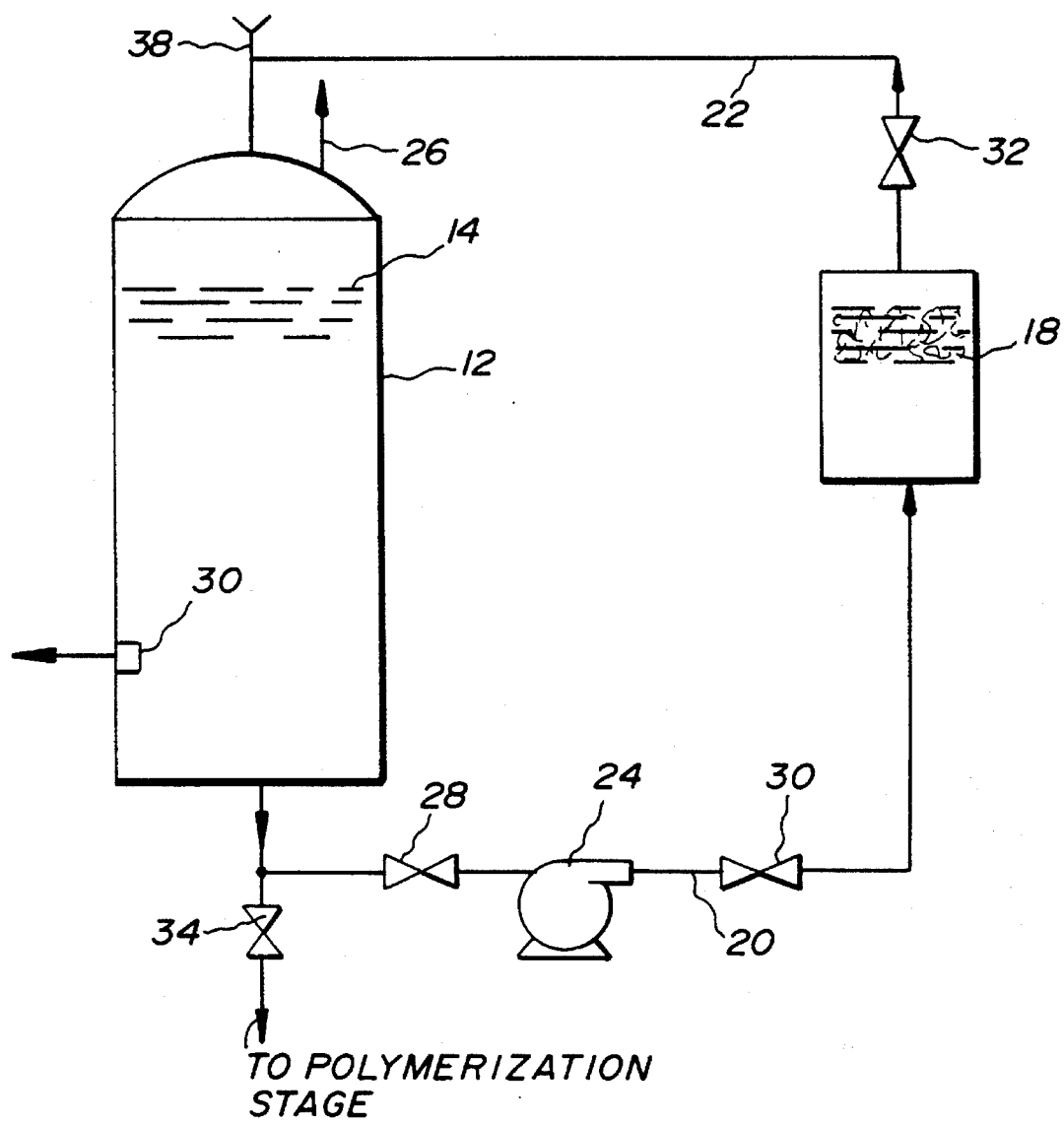
FIG. 1 is a flow diagram illustrating apparatus for desiccant drying by circulation into and out of a holding tank.

A detailed description of the process for the polymerization of cyclic diorganosiloxanes to form gums or the like is known in the art and is well described in Evans, U.S. Pat. No. 4,122,247, the teachings of which are incorporated herein by reference. In general the process comprises reacting a composition including a cyclic organopolysiloxane of 3–6 repeating units, including methyl, ethyl, vinyl or phenyl groups and alkyl, halogenated alkyl and cycloakyl groups with 3 to 8 carbon atoms and cyclic polysiloxane of 3–6 repeating units including methyl, ethyl, vinyl or phenyl groups. The reaction takes place in the presence of an akali metalhydroxide catalyst complexed with a low molecular weight polymer of ethylene oxide or a silonate of alkaline metal hydroxide complexed with a low molecular weight polymer of ethylene oxide. The reaction is neutralized after equilibrium has been reached. An important feature noted in the Evans patent is that it has been found that if there is substantially more than 10 ppm of water present in the cyclic siloxanes, then the desired low molecular weight oil or high molecular weight diorganosiloxane homo or copolymer gum will not be found in commercially attractive yields.

High molecular weight polymers can be derived from fluoro silicone cyclic trimers by desiccant drying the trimers by intimate contact with a sufficient quantity of silica gel desiccant under a blanket of nitrogen at about ambient temperature. The dried trimer is then polymerized at an elevated temperature for an appropriate time. In a particular exemplary implementation of the invention, a fluorosilicone cyclic trimer such as 1,3,5-trimethyl-1,3,5-tris(3,3,3-trifluoropropyl) cyclotrisiloxane (about 133 parts) was agitated with one part of indicating silica gel, amorphous silicon dioxide, indicating type GRADE 44, CAS #1343-98-2, 3–8 mesh, Davison Chemical Div., W. R. Grace & Co., $SiO_2 \cdot XH_2O + CaCl_2$. The mixture was agitated under a blanket of nitrogen at 30°–40° C. for four hours. The dried trimer was then polymerized at 125°–140° C. for a period of four hours. Absorption drying over anhydrous or desiccant silica gel is a practical process because the material can absorb up to about 28% of its weight before saturation is indicated.

In the above example, the desiccant contains a cobaltous chloride which turns pink when saturated. The desiccant silica gel has a porous intermolecular structure which provides a vast network of microscopic pores to attract and hold water by physical adsorption and capillary condensation. The silica gel is unlike a molecular sieve because it is shock resistant and not friable. If desired, the desiccant gel may be regenerated by subjecting it to elevated temperatures or it may be discarded.

Table 1 is an illustration of results obtained by polymerization of a fluorosilicone cyclic trimer. The first column lists selected starting materials, some relevant properties and conditions. The second column lists the amount of each starting material and the resulting properties with no drying. The third column represents the results with azeotropic drying. The fourth column represents results from the above example after drying in accordance with the present invention, termed adsorption drying.

TABLE 1

POLYMERIZATION OF FLUOROSILICONE CYCLIC TRIMER

|  | No Drying | Azeotrope Drying | Adsorption Drying (Si gel)[7] |
|---|---|---|---|
| Moisture Content[3] | 92 ppm | 92 ppm | <7.0 ppm |
| FS trimer | 400.0 g. | 445 (34 g xs)[4] | 400.0 g. |
| [ViSi(Me)O]$_3$ | 0.75 g. | 0.78 g. | 0.75 g. |
| Chain modifier[5] | 5.10 g. | 5.30 g. | 5.10 g. |

TABLE 1-continued

POLYMERIZATION OF FLUOROSILICONE CYCLIC TRIMER

|  | No Drying | Azeotrope Drying | Adsorption Drying (Si gel)[7] |
|---|---|---|---|
| Sodium fluoro-silanolate | 0.14 g. | 0.15 g. | 0.14 g. |
| Volatiles content | 1.96 | 0.5% | 0.1% |
| WP (3') | 196 | 212 | 256 |
| Vinyl Content[6] | 0.073 wgt % | 0.07 wgt % | 0.07 wgt % |
| $N_2$ SPG (25° C.) | — | 1.3035 | 1.3066 |

[3]Moisture content by Zerewitinoff method, gaseous evolution of methane via reaction of Grignard with water.
[4]Excess trimer (34 grams) was sparged out with anhydrous nitrogen while at 150° C.
[5]A 10:1 mixture by wgt of vinyl terminated FS-PDMS copolymeric fluid with a vinyl content of 1.25 wgt % plus silanol terminated fluorosilicone telomeric fluid having OH content of @ 6.25 wgt %.
[6]Total vinyl content as measured by FTIR.
[7]Mohn Hardness: 5 (Davidson Chem. Div.).

It can be seen from the table that drying in accordance with the present invention results in increased Williams Plasticity (WP) from 196 without drying and 212 with azeotropic drying to 256 with adsorption drying.

Tables 2 and 3 below illustrate the use of adsorption drying of fluorosilicone cyclic trimers to prepare silanol terminated and vinyl terminated HMW polymers. The monomer is pumped through a vertical column containing 40 pounds of silica gel at a rate of 3 gallons per minute. Table 2 illustrates silanol terminated FS polymers and Table 3 illustrates vinyl terminated FS polymers.

TABLE 2

SILANOL TERMINATED FS POLYMERS
Polymerization 2 hrs/130–140° C.
Vinyl range 0-05–0.095 wgt. %
Williams Plasticity
Trimer Level 800 lbs.

| Drying Time | $H_2O$ Content. ppm | Chain Stopper | WP 3' | [ViSi(Me)O]$_3$ | Vinyl Content | Volatiles |
|---|---|---|---|---|---|---|
| 0 hrs. | 45 | 3.10 | 310 | 860 grams | 683 ppm | 1.1% |
| 4 | 27 | 11.5 | 238 | 907 | 543 | 1.2 |
| 5 | 19 | 13.8 | 230 | 956 | 600 | 1.2 |
| 4.5. | 23 | 16.0 | 210 | 955 | 620 | 1.2 |
| >4 | 20 | 18.0 | 146 | 954 | 711 | 1.05 |

TABLE 3

VINYL TERMINATED FS POLYMERS

| Drying Time hrs. | $H_2O$,ppm | Vinyl Chain Stp | Silanol Chain Stp | WP (3') | Yield. lbs. |
|---|---|---|---|---|---|
| 3.0 | 22 | 5.0 lbs | 0.4 lbs | 203 | 812 |
| 3.0 | 28 | 5.0 | 0.4 | 214 | 818 |
| 3.0 | 30 | 5.0 | 0.5 | 197 | 850 |
| 4.0 | 28 | 5.0 | 0.5 | 177 | 862* |
| 3.0 | 21 | 5.0 | 0.5 | 196 | 828 |
| 3.0 | 21 | 5.0 | 0.5 | 196 | 828 |
| 4.5 | 22 | 5.0 | 0.5 | 196 | 840 |
| 4.5 | 25 | 5.0 | 0.5 | 220 | 842 |

*Vessel not properly dried before charging with monomer and imputs.

It has been found that molecular weight control and chain end moiety control resulting from drying in a desiccant silica gel is enhanced as a result of the invention. The polymers display a relatively narrow range of molecular weight with better molecular weight control than formerly obtained in the art.

The dispersion index $D_i$, which is a measure of the variation in molecular weight above the target is defined as:

$$D_i = N_w/N_n$$

where $N_w$ = weight average of all molecular weights; and $N_n$ = number average of molecular weights.

In accordance with the invention batch to batch $D_i$ may be more closely controlled than in prior arrangements. For good results $D_i$ is less than about 1.8; it is about 1.5 but is more preferably less than about 1.2.

A relatively simple way to characterize molecular weight variation is to the measure Williams Plasticity (WP) of the resulting polymer. WP is the amount by which the thickness of a sample of a given volume is reduced when subjected to a uniform force (weight) for a given amount of time. Prior art drying methods result in a batch to batch variation in WP of about 140–220 or 80 points. The batch to batch variation in WP of the resulting polymers after predrying the monomers with a desiccant silica gel in accordance with the present invention is about 170–220 or about 50 points. The narrow dispersion of the molecular weight as evidenced by the reduced variation in WP has a positive impact upon the producibility and quality resulting heat cured rubber compounds. The variation is less than about 30% and is preferably less than 23%.

FIG. 1 illustrates a simplified flow diagram of an exemplary apparatus for implementing the present invention in a batch type circulating system. A trimer holding tank 12 contains a selected level of starting materials or monomers 14. The monomers 14 have a water content which is ultimately to be reduced to a selected level. A column 16 contains a supply of finely divided cobaltous indicating silica desiccant gel 18. The tank 12 and the column 16 are interconnected by circulating lines 20 and 22. A circulating pump 24 circulates material between the tank 12 and column 16 as illustrated. A vent is provided in the holding tank 12 and various check valves 28, 30 and 32 control flow through the system. Monomers 14 are circulated through the silica gel 18 and moisture is removed from the monomers by adsorption drying. A moisture sensor 36 located in the tank 12 provides an output signal indicative of the water content in the monomers after a selected drying period. When the water content reaches a selected level, the various check valves are reconfigured and the contents of the tank 12 is directed to a polymerization stage, not shown, through the check valve 34. Likewise, at the end of the drying cycle, the desiccant gel 18 may be replaced with a fresh supply and a new supply of monomers 14 may be provided.

Figure 2:
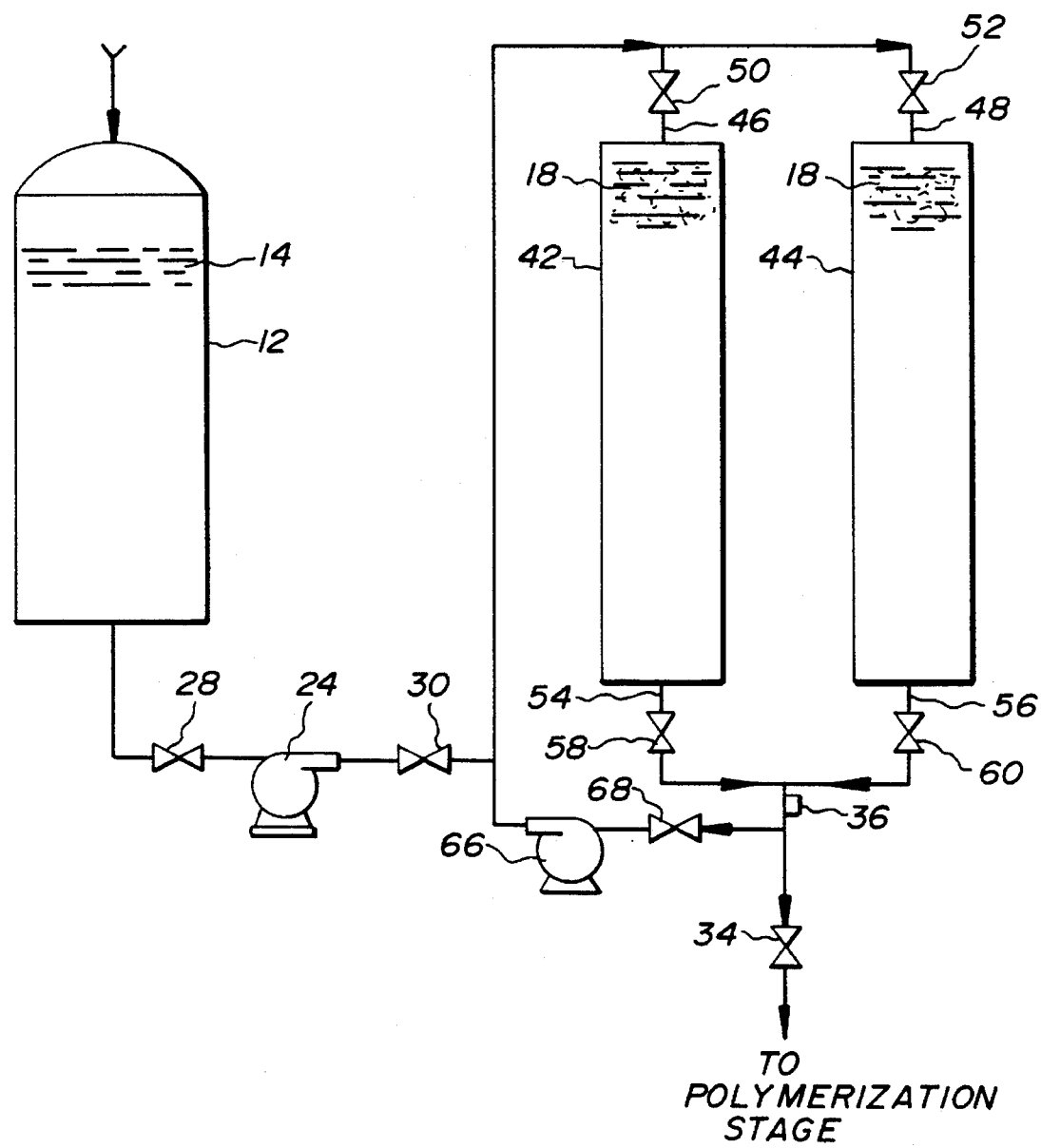
FIG. 2 is a flow diagram illustrating an apparatus for once through processing by means of reaction columns.

FIG. 2 illustrates an alternative embodiment of the invention comprising a once through system in which similar elements are labelled with the same reference numerals as in FIG. 1. In the arrangement of FIG. 2, monomers 14 are coupled by an input line 40 to a pair of drying columns 42 and 44, each of which is packed with a silica gel desiccant 18. Each of the columns 42 and 44 have respective inlets 46 and 48 controlled by check valves 50 and 52 and outlets 54 and 56 governed by check valves 58 and 60. In the embodiment illustrated, the monomers 14 may be coupled to one of the columns 42 and 44 while the other stands idle. The monomers are passed through the drying column, for example column 42, whereupon the water is adsorbed in the silica gel 18. When the gel is saturated in the column 42, the check valves 50 and 58 are closed and the check valves 52 and 60 to the column 44 are open so that the process may be operated continuously. Thereafter, the column 42 and its contents may either be replaced or regenerated. In the meantime, a commonly coupled outlet 62 of columns 42 and 44 feeds a polymerization stage, not shown. In this way, continuous processing of the material may be effected for more efficient operation. Appropriate control for recirculating the dried monomers may be provided in the event that the level of adsorption is insufficient. For example, the sensor 36 may be located in the outlet line 62 whereby recirculation to the inlet line 40 may be achieved via recirculation line 64 including a pump 66 and check valve 68. The arrangement of FIG. 2 is a most efficient apparatus performing the method of the present invention. It should be understood however, that the arrangement of FIG. 1 can be effectively utilized in existing systems at a relatively moderate cost.

In either case, the drying step takes place separate from polymerization. Thus, the disadvantages of combined polymerization and drying are eliminated. Further, the process is simplified because one batch of monomer can be dried as another is polymerized, thereby promoting turn key implementations.

Table 4 represents laboratory data for drying fluorosilicone trimer by contact with silica gel.

TABLE 4

Adsorption Drying of Fluorosilicone Trimer Via Contact with Silica Gel

| | Silica Gel Content | |
| --- | --- | --- |
| Time* (Minutes) | 10.0 GR/100 GR of Trimer Moisture Content PPM $H_2O$ | 3.0 GR/100 GR of Trimer Moisture Content PPM $H_2O$ |
| 0 | 98 | 94 |
| 30 | 66 | — |
| 60 | 42 | 53 |
| 90 | — | — |
| 120 | 7.0 | 34 |
| 180 | — | 17 |

*Agitated under nitrogen atmosphere while at 30–40° C.

Figure 3:
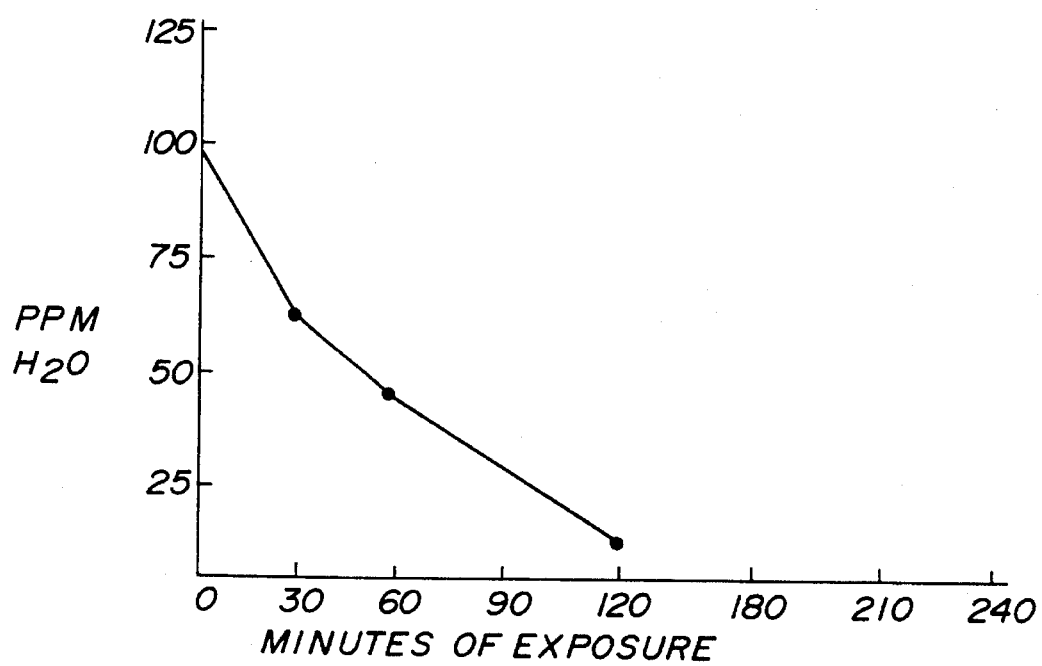
FIGS. 3 and 4 are exemplary plots illustrating the water content of a fluorosilicone cyclic trimer in ppm versus minutes of exposure to a silica gel.
Figure 4:
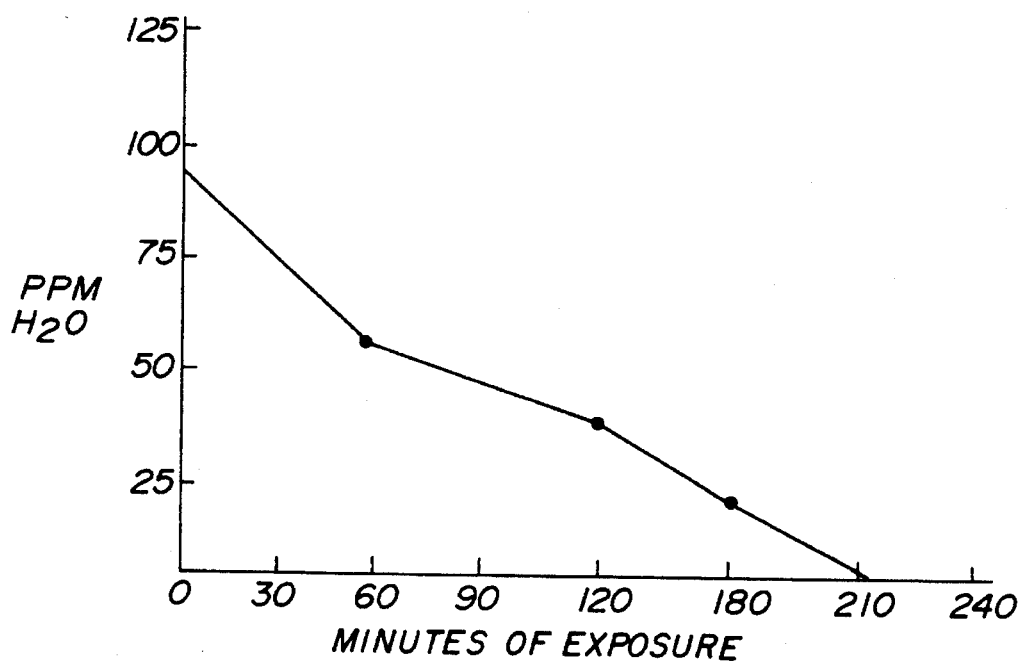

The data represents adsorption drying of fluorosilicone cyclic trimer with silica gel (3–8 mesh) grade 44 indicating type (cobaltous chloride) Davidson Chemical Division, W.R. Grace & Co., at 30°–40° C. in a $N_2$ atmosphere. In FIG. 3, the ratio of silica gel to trimer from table is 10/100 (10%). In FIG. 4, the ratio is 3/100 (3%). As can be appreciated from the data, the higher ratio of 1/10 gel to trimer reduced the drying time by at least one hour to achieve a moisture content of less than 10 ppm. Of course, lower levels of desiccant can be used if a lower drying time is not objectionable.

While there has been described what at present are considered to be the preferred embodiments of the present invention, it will be apparent to those skilled in the art that various changes may be made therein without departing from the invention and it is intended in the appended claims to cover such changes and modifications that fall within the true spirit and scope of the invention.

What is claimed is:

1. A process for removing water contamination from a cyclic diorganosiloxanes monomer, comprising:

(a) contacting the cyclic diorganosiloxane monomer with a silica gel; and (b) drying the monomer by absorbing the water contamination onto the silica gel, wherein the silica gel is present in a quantity sufficient to adsorb water whereby the concentration of water present in the monomer after removal of the water from the monomer is less than about 10 ppm and wherein the adsorption of water is conducted at a temperature ranging from about 30° to about 40° C. for a period of about four hours, whereby the monomer is not polymerized by said adsorption and whereby when said monomer is polymerized a high molecular weight polymer having a narrow range of molecular weights results wherein said molecular weight range of said high molecular weight polymer has a dispersion index below about 1.8.

2. The process of claim 1, wherein the ratio of silica gel to monomers is about at least 3%.

3. The process of claim 2, wherein the ratio is about 10%.

4. The process of claim 1, wherein the diorganosiloxanes are mixed with chain stoppers comprising hydroxyl, methyl, chlorofluorocarbons and vinyl.

5. The process of claim 1 wherein said drying step is conducted under an atmosphere of nitrogen.

* * * * *